US009451888B1

(12) United States Patent
Bernstein

(10) Patent No.: US 9,451,888 B1
(45) Date of Patent: Sep. 27, 2016

(54) METHOD AND APPARATUS FOR DETERMINATION OF LEFT VENTRICULAR STROKE VOLUME AND CARDIAC OUTPUT USING THE ARTERIES OF THE FOREARM

(71) Applicant: Cordeus, Inc., Rancho Santa Fe, CA (US)

(72) Inventor: Donald P. Bernstein, Rancho Santa Fe, CA (US)

(73) Assignee: CORDEUS, INC., Rancho Santa Fe, CA (US)

( * ) Notice: Subject to any disclaimer, the term of this patent is extended or adjusted under 35 U.S.C. 154(b) by 0 days.

(21) Appl. No.: 14/728,959

(22) Filed: Jun. 2, 2015

Related U.S. Application Data

(60) Provisional application No. 62/139,614, filed on Mar. 27, 2015.

(51) Int. Cl.
| | |
|---|---|
| *A61B 5/02* | (2006.01) |
| *A61B 5/029* | (2006.01) |
| *A61B 5/0295* | (2006.01) |
| *A61B 5/00* | (2006.01) |

(52) U.S. Cl.
CPC ........... *A61B 5/029* (2013.01); *A61B 5/02028* (2013.01); *A61B 5/0295* (2013.01); *A61B 5/4884* (2013.01); *A61B 5/6824* (2013.01); *A61B 5/6832* (2013.01); *A61B 5/7278* (2013.01); *A61B 5/742* (2013.01)

(58) Field of Classification Search
CPC .................. A61B 5/02028; A61N 1/36571
See application file for complete search history.

(56) References Cited

U.S. PATENT DOCUMENTS

| | | | |
|---|---|---|---|
| 4,450,527 A | 5/1984 | Sramek | |
| 5,469,859 A | 11/1995 | Tsoglin et al. | |
| 5,735,284 A | 4/1998 | Tsoglin | |
| 5,782,774 A | 7/1998 | Shmulewitz | |
| 6,292,689 B1 | 9/2001 | Wallace | |
| 6,361,501 B1 * | 3/2002 | Amano | A61B 5/02028 600/485 |
| 6,511,438 B2 | 1/2003 | Bernstein | |

(Continued)

OTHER PUBLICATIONS

Targett, et al., "Simultaneous Doppler Blood Velocity Measurements . . . Subjects," Cardiovascular Research, pp. 394-399, 1985.

(Continued)

*Primary Examiner* — William Levicky
(74) *Attorney, Agent, or Firm* — DLA Piper LLP (US)

(57) ABSTRACT

An apparatus and method for determining stroke volume by bioimpedance from a person that includes two or more spaced apart alternating current flow electrodes positionable on a person's forearm, two or more spaced apart voltage sensing electrodes positionable on the person's forearm and between the alternating current flow electrodes, an alternating current source providing an alternating current to the current flow electrodes, a voltmeter configured to generate a voltage signal from a voltage sensed by the voltage sensing electrodes, and a processing unit configured to determine a stroke volume (SV) using the voltage signal and at least one of two equations that include, among other terms, the person's weight, a peak time rate of change of a transradioulnar impedance pulse variation ($dZ/dt_{max}$), a transradioulnar quasi-static base impedance ($Z_0$), a systolic flow time ($T_{SF}$), and a volume conductor (Vc).

19 Claims, 5 Drawing Sheets

(56) References Cited

U.S. PATENT DOCUMENTS

| | | |
|---|---|---|
| 7,261,697 B2 | 8/2007 | Bernstein |
| 7,740,590 B2 | 6/2010 | Bernstein |
| 7,806,830 B2 | 10/2010 | Bernstein |
| 2006/0009710 A1* | 1/2006 | Bernstein ............ A61B 5/02028 600/547 |
| 2007/0219059 A1* | 9/2007 | Schwartz ............. A61B 5/0205 482/8 |

OTHER PUBLICATIONS

Wang, et al., "Evaluation of Changes in Cardiac Output From the Electrical . . . Forearm," Physiol Meas. 28, IOP Publishing, pp. 989-999, 2007.

Bernstein, "Impedance Cardiography: Pulsatile Blood Flow and the Biophysical . . . Equations," Journal of Electrical Bioimpedance, vol. 1, pp. 2-17, 2010.

Bassett, et al., "Limiting Factors for Maximum Oxygen Uptake and . . . Performance," Medicine & Science in Sports & Exercise, pp. 70-84, 2000.

Bernstein, et al., "Stroke Volume Equation for Impedance Cardiography," Medical & Biological Engineering & Computing, vol. 43, pp. 443-450, 2005.

K. Beck, et al., "Relationship Between Cardiac Output and Oxygen Consumption During Upright Cycle Exercise in Healthy Humans," J. Appl. Physiol 101:1474-1480, 2006.

Jan Nyboer, "Electrical Impedance Plethysmography," Circulation, vol. II, pp. 811-821, Dec. 1950.

Stringer, et al., "Cardiac Output Estimated Noninvasively From Oxygen Uptake During Exercise," J. Appl. Physiol 82:908-912, 1997.

Henry, et al., "Stroke Volume Obtained From the Brachial Artery Using Transbrachial Electrical Bioimpedance Velocimetry," IEEE. pp. 142-145, 2012.

Lynn, et al., "Arm and Wrist Surface Potential Mapping for Wearable ECG Rhythm Recording Devices: a pilot clinical study," IOP Publishing Ltd., Sensors & their Applications XVII, Journal of Physics: Conference Series 450, pp. 1-8, 2013.

Zambanini, et al., "Wave-energy Patterns in Carotid, Brachial, and Radial Arteries: A noninvasive Approach Using Wave-intensity Analysis," Am J Physiol Heart Circ Physiol 289, pp. 270-276., Feb. 2005.

Wang, et al., "Development of Forearm Impedance Plethysmography for the Minimally Invasive Monitoring of Cardiac Pumping Function," J. Biomedical Science and Eng., pp. 122-129, 2011.

Bernstein, et al., "Validation of Stroke Volume and Cardiac Output by Electrical Interrogation of the Brachial Artery . . . Error," Journal of Clinical Monitoring and Computing, ISSN 1387-1307, Feb. 2015.

Bernstein, et al., "Stroke Volume Obtained by Electrical Interrogation of the Brachial Artery . . . Velocimetry," Institute of Physics and Eng. in Medicine, Physiol. Meas. 33, pp. 629-649, 2012.

Rodriguez, et al., "Non-invasive Estimate of Cardiac Output During Exercise Based on Impedance Cardiography and Oxygen Uptake in the Elderly," Arq Bras Cardiol 2007; 88(1): pp. 71-75.

Chemla, et al., "Blood Flow Acceleration in the Carotid and Brachial Arteries . . . Resistance," Fundamental & Clinical Pharmacology 1996:10: pp. 393-399.

Weissler, et al., "Systolic Time Intervals in Heart Failure in Man," Circulation, vol. XXXVII No. 2, pp. 149-159, 1968.

Lepretre, et al., "Effect of Exercise Intensity on Relationship Between . . . Output," American College of Sports Medicine, pp. 1357-1363, 2004.

Goncalves, et al., "Non-contact Wearable Single Forearm Cardiac Biopotential Acquisition Device," Journal of Physics: Conference Series 459, pp. 1-6, 2013.

\* cited by examiner

METHOD AND APPARATUS FOR DETERMINATION OF LEFT VENTRICULAR STROKE VOLUME AND CARDIAC OUTPUT USING THE ARTERIES OF THE FOREARM

RELATED APPLICATIONS

This application claims the benefit of U.S. Provisional Application No. 62/139,614, filed Mar. 27, 2015, and which is incorporated herein by reference.

FIELD OF THE INVENTION

This present invention relates to the determination of the volumetric output of the left ventricle of a person's heart per beat, otherwise known as stroke volume (SV), measured in milliliters (mL), and the volumetric output of the left ventricle of a person's heart per minute, known as cardiac output (CO), measured in liters per minute (L·min$^{-1}$). More particularly, this invention relates to the determination of SV and CO by transradial-ulnar electrical (bioimpedance) velocimetry (TRUBEV).

BACKGROUND OF THE INVENTION

All methods, apparatus, and inventions related to the measurement of SV/CO by the electrical bioimpedance method have heretofore been implemented by means of:
  Transthoracic method, known as transthoracic electrical bioimpedance cardiography, or impedance cardiography (ICG), U.S. Pat. No. 4,450,527 A.
  Transthoracic electrical (bioimpedance) velocimetry, U.S. Pat. No. 6,511,438 B2.
  Total or whole body electrical bioimpedance plethysmography method, also known as total (whole) body electrical bioimpedance cardiography, U.S. Pat. No. 5,469,859, U.S. Pat. No. 5,735,284.
  Transbrachial electrical (bioimpedance) velocimetry, U.S. Pat. No. 7,261,697, B2, U.S. Pat. No. 7,740,590 B2, U.S. Pat. No. 7,806,830 B2.
  Endotracheal cardiac output, U.S. Pat. No. 5,782,774, U.S. Pat. No. 6,292,689.

Apart from the transthoracic and transbrachial velocimetric techniques, all prior methods ascribe a pure volumetric origin for the time-dependent primary impedance change $\Delta Z(t)$ (ohm, $\Omega$) and its peak time rate of change (first time-derivative) $dZ(t)/dt_{max}$, originally thought to be measured in $\Omega \cdot s^{-1}$. The two most widely used methods ascribing a volumetric (plethysmographic) etiology for both $\Delta Z(t)$ and $dZ/dt_{max}$ include the Nyboer-Kubicek and Sramek-Bernstein techniques, which differ with respect to their individual spot or band-electrode configurations on the thorax (chest) and their respective SV equations (Bernstein et al. Stroke volume equation for impedance cardiography. *Med Biol Eng Comput* 2005; 43:443-50; Bernstein D P, Impedance Cardiography: Pulsatile blood flow and the biophysical and electrodynamic basis for the stroke volume equations. *J Electr Bioimp.* 2010; 1:2-7) and as disclosed in Bernstein et al. U.S. Pat. No. 6,511,438 B2).

The aforementioned bioimpedance methods have been implemented for a variety of medical and non-medical purposes:
  Determination of CO in sick hospitalized patients.
  Cardiac pacemaker resynchronization therapy.
  Cardiac rehabilitation for post myocardial infarction and heart failure patients.
  Exercise physiology using the transthoracic methods.
  Efficacy of intense aerobic training as a surrogate for maximal oxygen consumption.
  Effect of medications on the cardiovascular system.

Studies involving the radial/ulnar arteries of the forearm include:
  Nyboer (Nyboer J. Electrical impedance plethysmography; a physical and physiologic approach to peripheral vascular study. *Circulation* 1950; 2:811-21) demonstrated that electrical impedance changes ($\Delta Z$) of the forearm correlated with volumetric strain gauge approximations of volume changes in the vessels of the forearm.
  Wang et al. (Wang et al. Evaluation of changes in cardiac output from electrical impedance changes of the forearm. *Physiol Meas.* 2007; 28:989-99) and Wang et al. (Wang et al. Development of forearm impedance plethysmography for minimally invasive monitoring of cardiac pumping function. *Journal of Biomechanical Science and Engineering.* 2011; 14:122-29) demonstrated that, the change in magnitude and percent change in the magnitude of forearm of $\Delta Z$ and the change in magnitude and percent change in area beneath the $\Delta Z$ were highly correlated with the change in magnitude and percent change in magnitude of measured stroke volume (SV). Neither the magnitude of $\Delta Z$ or area beneath the $\Delta Z$ waveform correlated well with measured SV.
  Targett et al. (Targett R et al. Simultaneous Doppler blood velocity measurements from the aorta and radial artery in normal human normal subjects. *Cardiovasc Res.* 1985; 19:394-399) demonstrated that peak radial artery blood acceleration has a constant relationship with peak aortic blood acceleration, regardless of age.
  Chemla et al. (Chemla et al. Blood flow acceleration in the carotid and brachial arteries of healthy volunteers: respective contributions of cardiac performance and local resistance. *Fundam Clin Pharmacol* 1996; 10:393-99) noted that peak brachial artery and peak radial artery acceleration were of similar magnitudes.
  Zambanini et al. (Zambanini et al. Wave energy in carotid, brachial and radial arteries: a noninvasive approach using wave intensity analysis. *Am J Physiol Heart Circ Physiol.* 2005; 289:H270-H276) demonstrated that the magnitude of brachial and radial artery velocities and peak slope of the velocity waveforms were nearly identical.

BRIEF SUMMARY OF THE INVENTION

It has been discovered that SV can be obtained from the radial artery with equivalent accuracy as that of the transbrachial approach. Bernstein et al. Stroke volume obtained by electrical interrogation of the brachial artery: transbrachial electrical bioimpedance velocimetry. *Physiol Meas* 2012; 33:629-49, and Bernstein et al. Validation of stroke volume and cardiac output by electrical interrogation of the brachial artery in normals; assessment of strengths, limitations, and sources of error. *J Clin Monit Comput* 2015; 15 Feb. 2015 [Epub ahead of print]. The studies, especially those of Wang et al and Wang et al (vide supra) did not investigate the correlation of absolute SV with the peak first time-derivative of forearm $\Delta Z$, namely, forearm $dZ/dt_{max}$. They, therefore, were unable to transform $dZ/dt_{max}$, an acceleration analog, to ohmic mean velocity, which is necessary for SV determination (Bernstein et al. Stroke volume equation for impedance cardiography. *Med Biol Eng Com-*

*put* 2005; 43:443-50). Absolute SV cannot be determined by implementation of un-signal processed ΔZ.

While the present invention would be appropriate for any of the above implementations, it is specifically designed, but not limited to use in aerobic fitness training, such as with a stationary exercise bicycle, elliptical pedaling device, treadmill, or any other stationary exercise machines. Cardiac output is a useful monitoring variable in assessing aerobic fitness, because it virtually parallels oxygen consumption ($VO_2$). Maximum oxygen consumption ($VO_{2\ max}$), the holy grail of aerobic cardiorespiratory fitness, is near-linearly related to maximum cardiac output. Maximum cardiac output, in turn, is the ultimate expression of cardiovascular performance. (Cooke G A et al. Physiologic reserve: development of a noninvasive method and first estimates in man. *Heart* 1998; 79:289-294; Beck K C et al. Relationship between cardiac output and oxygen consumption during upright cycle exercise in healthy humans. *J Appl Physiol* 2006; 101:1474-1480; Rodrigues M N, et al. Noninvasive estimate of cardiac output during exercise-based on impedance cardiography and oxygen uptake in the elderly. *Arq Bras Cardiol* 2007; 88:71-75; Lepretre P M et al. Effect of exercise intensity on relationship between $VO_{2\ max}$ and cardiac output. *Sci Med Sports Exerc* 2004; 36:1357-1363; Bassett D R et al. Limiting factors for maximum oxygen uptake and determinants of endurance performance. *Med Sci Sports Exerc* 2000; 32:70-84.) Advantages of obtaining stroke volume and cardiac output from arteries of the forearm, namely from the radial and ulnar arteries, considered in the aggregate, include the following:

- Less motion of forearm than that of the thorax or upper arm when used with a stationary exercise bicycle with fixed handlebars, an elliptical pedaling device, or treadmill with stationary arm rests, therefore producing less motion signal artifact.
- Electrodes on forearm are more easily placed and affixed by user-subject than either the transthoracic or upper arm transbrachial electrode configurations.
- Electrodes on forearm are more closely tethered directly by electric cable or wirelessly to a signal acquisition and processing module on the wrist or a signal acquisition and processing module directly connected to a peripheral devices, such as a stationary bicycle, treadmill, elliptical pedaling device, or any other exercise device in contact with the subject.
- The onset of flow, otherwise known as point B on dZ/dt, is more easily identified than that from the transthoracic bioimpedance methods.
- Forearm applications of the velocimetric bioimpedance technique are affected less by respiratory variations in ΔZ, the primordial impedance change, and its peak time rate of change, transradioulnar $dZ/dt_{max}$, in comparison with the chest (thorax) or upper arm (brachium).
- Forearm impedance changes will not be affected by excess intrathoracic, extravascular lung water (pulmonary edema) or peripheral lower arm edema, when used in the intended healthy population.
- Exemplary waveforms obtained from the forearm in healthy humans allow precise identification of point B (onset of flow) and the second zero crossing of dZ/dt (point X, termination of flow), the temporal interval separating the two points, representing systolic flow time (SFT), which is equivalent to left ventricular ejection time (LVET, $T_{LVE}$).

The present invention is an apparatus and method for determining stroke volume (SV) and cardiac output (CO) by means of transradioulnar bioimpedance velocimetry from a healthy human subject, including two spaced apart alternating current flow electrodes, positionable on a persons lower arm, two spaced apart voltage sensing electrodes on the lower arm between the two alternating current flow electrodes, an alternating current source electrically connected to the current flow electrodes, a voltmeter connected to the voltage sensing electrodes, and a signal processing unit in communication with the voltage sensing electrodes. The processing unit is capable of using a voltage sensed by the voltage sensing electrodes to calculate a peak value of the first time-derivative of a cardiogenically induced impedance pulse variation of the subject's lower arm and to determine therefrom a stroke volume (SV) of the subject.

In another aspect of the present invention, a method of determining SV by bioimpedance from a person includes positioning two or more spaced apart alternating current flow electrodes on a subject, positioning two or more voltage sensing electrodes on the subject and between the current flow electrodes, providing an alternating current flow (I(t)) of high frequency (50-100 kHz) and small amplitude (2-4 mA) through the current flow electrodes generating a current field between the voltage sensing electrodes within the current field, measuring a voltage (U(t)) between the voltage sensing electrodes within the current field, calculating a peak value of the first time-derivative, transradioulnar $dZ/dt_{max}$.

Other objects and features of the present invention will become apparent by review of the specification, claims and appended figures.

An apparatus for determining stroke volume by bioimpedance from a person can include two or more spaced apart alternating current flow electrodes positionable on a person, two or more spaced apart voltage sensing electrodes positionable on the person and between the alternating current flow electrodes, an alternating current source electrically connectable to the alternating current flow electrodes, a voltmeter electrically connectable to the voltage sensing electrodes and configured to generate a voltage signal from a voltage sensed by the voltage sensing electrodes and a processing unit electrically connectable with the voltmeter and configured to determine a stroke volume (SV) using the voltage signal and the following equation:

$$SV = [a^n \cdot W^b] \cdot \left[ \frac{k_1 k_2}{(dZ/dt_{max} \cdot Z_0^{-1})^{0.5}} \right] \cdot \left[ \frac{dZ/dt_{max}}{Z_0} \right] \cdot T_{SF}$$

The term a is at least 5 and no greater than 10, n is at least 2 and no greater than 4, W is the person's weight, b is at least 1 and no greater than 2, $k_1 \cdot k_2$ collectively are a dimensionless constant at least 0.04 and no greater than 0.3, $dZ/dt_{max}$ is a peak time rate of change of a transradioulnar impedance pulse variation, $Z_0$ is a transradioulnar quasi-static base impedance, $T_{SF}$ is a systolic flow time, and Vc is $cM^d$ where c is at least 30 and no greater than 50, M is the person's weight and d is at least 1 and no greater than 2.

A method of determining stroke volume by bioimpedance from a person can include positioning two or more spaced apart alternating current flow electrodes on the forearm of a person, positioning two or more spaced apart voltage sensing electrodes on the forearm of the person and between the alternating current flow electrodes, providing an alternating current flow through the alternating current flow electrodes, measuring a voltage between the voltage sensing electrodes, and determining a stroke volume (SV) using the measured voltage and the following equation:

$$SV = [a^n \cdot W^b] \cdot \left[ \frac{k_1 k_2}{(dZ/dt_{max} \cdot Z_0^{-1})^{0.5}} \right] \cdot \left[ \frac{dZ/dt_{max}}{Z_0} \right] \cdot T_{SF}$$

The term a is at least 5 and no greater than 10, n is at least 2 and no greater than 4, W is the person's weight, b is at least 1 and no greater than 2, $k_1 \cdot k_2$ collectively are a dimensionless constant at least 0.04 and no greater than 0.3, $dZ/dt_{max}$ is a peak time rate of change of a transradioulnar impedance pulse variation, $Z_0$ is a transradioulnar quasi-static base impedance, $T_{SF}$ is a systolic flow time, and Vc is $cM^d$ where c is at least 30 and no greater than 50, M is the person's weight and d is at least 1 and no greater than 2.

Other objects and features of the present invention will become apparent by a review of the specification, claims and appended figures.

BRIEF DESCRIPTION OF THE DRAWINGS

The drawings accompanying and forming part of this specification are included to depict certain aspects of the invention. A clearer concept of the invention and of the components of the operation of systems provided with the invention, will become more readily apparent by referring to the exemplary, and therefore nonlimiting, embodiments illustrated in the drawings, wherein identical reference numerals or letters (i.e. A, B, C, etc.) designate the same components. The invention may be better understood by reference to one or more of these drawings in conjunction with the description presented herein. It should be noted that the features illustrated in the drawings are not necessarily drawn to scale.

DETAILED DESCRIPTION OF THE INVENTION

The invention and the various features and advantageous details thereof are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating preferred embodiments of the invention, are given by way of illustrations only and not by way of limitation. Various substitutions, modifications, additions an/or rearrangements within the spirit and/or scope of the underlying inventive concept will become apparent to those skilled in the art from this disclosure.

As used herein, the terms "comprises", "comprising", "includes", "including", "has", "having" or any other variation thereof, are intended to corner a non-exclusive inclusion. For example, a process, method, article, or apparatus that comprises a list of elements is not necessarily limited to only those elements but may include other elements no expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the pleural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Figure 1:
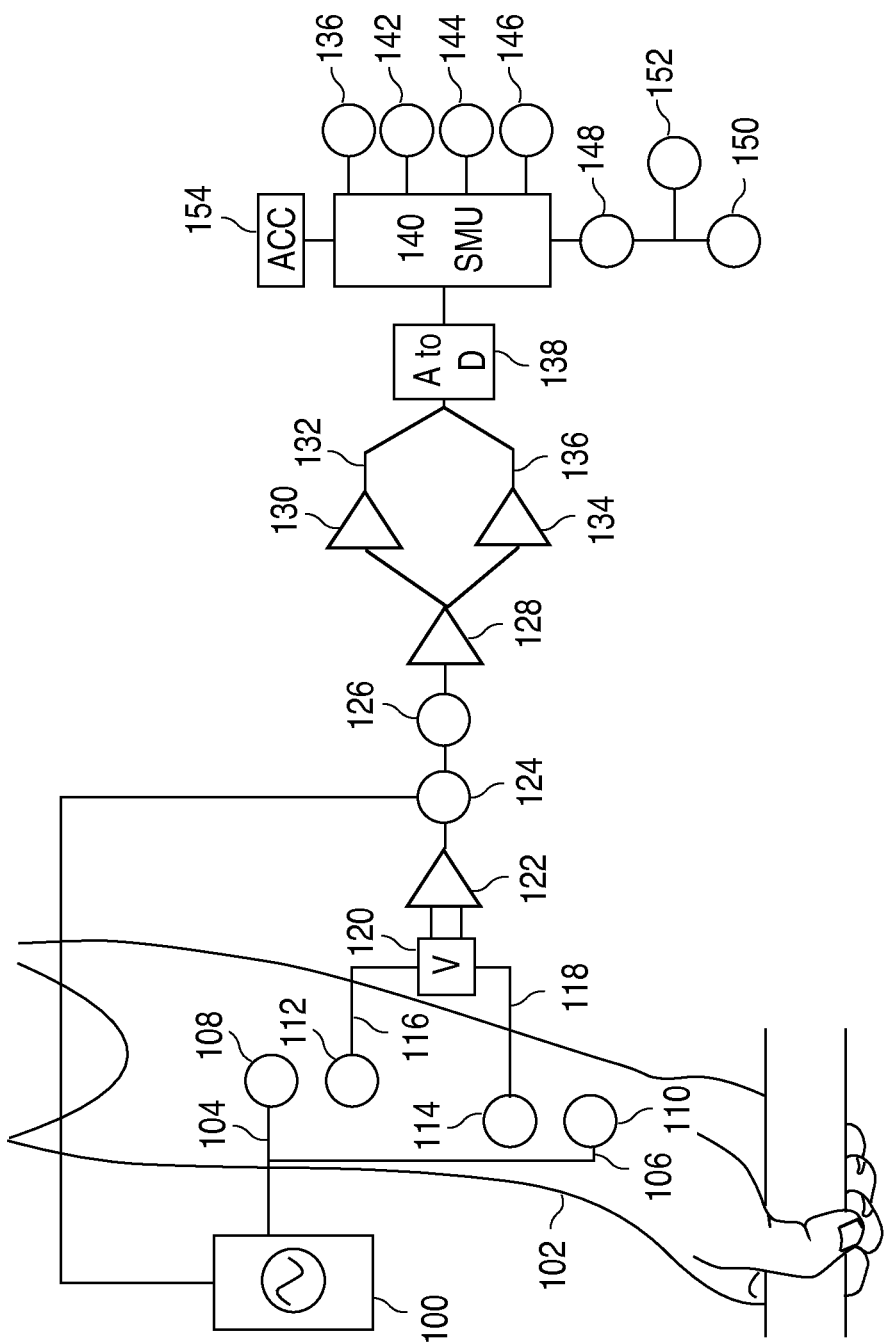
FIG. 1 is a plan view showing the stroke volume and cardiac output apparatus as applied to the person's forearm.

FIG. 1 shows placement of electrodes on a person's lower arm (forearm). A.C. (I) 100 is injected through a segment of the lower arm, otherwise known as the forearm 102, the AC 100 injected through a first current flow wire 104 operably connected to a first current flow proximal to the antecubital fossa and a second current flow wire 106 operably connected to a second current flow electrode 110 proximal to the wrist. A first voltage-sensing electrode 112 placed distal to the first current flow injector electrode 108 and a second voltage-sensing electrode 114 proximal and cephalad to the second current flow electrode 110. The first voltage sensing electrode 112 is operably connected to a first voltage-sensing wire 116 and the second voltage-sensing electrode 114 operably connected to a second voltage-sensing wire 118, where both voltage-sensing wires 116,118 are operably connected to a voltmeter 120. The voltmeter 120 is operably connected to a differential amplifier 122, where the voltage is fed from amplifier 122 to a voltage demodulator 124. The demodulated voltages undergo phase adjustment 126, and are then subject to noise reduction, fed into a low pass filter 128 (30 Hz) and then further fed into a high pass filter 130 (0.1 Hz) to yield oscillating voltage ΔZ 132 and through a second low pass filter 134 (10 Hz) yielding a static impedance voltage $Z_0$ 136. ΔZ 132 and $Z_0$ 136 are then fed into an analog to digital (A to D) converter 138, the A to D conversion signal is fed into a signal microprocessor unit (SMU) 140 where ΔZ 136 undergoes electronic differentiation to dZ/dt, where the peak value of dZ/dt is found $dZ/dt_{max}$ 142, the square root of $dZ/dt_{max}/Z_0$ is calculated, systolic flow time ($T_{SF}$) 144 is determined, and a volume conductor $V_C$ 146 is calculated from a person's body weight. From equations 1 and 3 discuss below, stroke volume (SV) 148 is calculated, and the cardiac output (CO) 150 calculated as the product of heart rate 152 and SV 148. Also shown is an accelerometer 154 operably connected within the signal microprocessor unit (SMU) 140.

Figure 2:
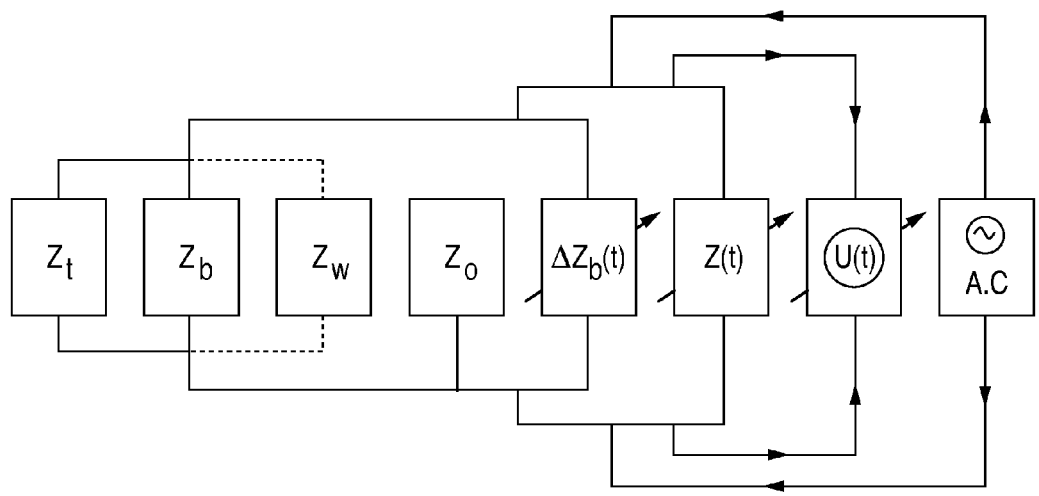
FIG. 2 is a schematic drawing of the transradioulnar impedance (Z(t)).

FIG. 2 is a schematic of the transradioulnar impedance (Z(t)), further comprising four elements. The three static elements include the impedance path through the adynamic tissues ($Z_t$), such as bone, muscle and connective tissue, the impedance path through the blood ($Z_b$), and interstitial water ($Z_w$). The parallel connection of these static and quasi-static ($Z_w$) impedances constitutes the transradioulnar base impedance, $Z_0$. Excluding the respiratory variation of Z ($\Delta Z_{resp}$), the parallel connection between $Z_0$ and the dynamic pulsatile component of the blood impedance/resistance ($\Delta Z_b(t)$) constitutes the total impedance of the forearm (Z(t)) between the voltage sensing electrodes. Shown are the alternating current flow input (AC, I(t)) and the time variable voltage output (U(t)).

Figure 3:
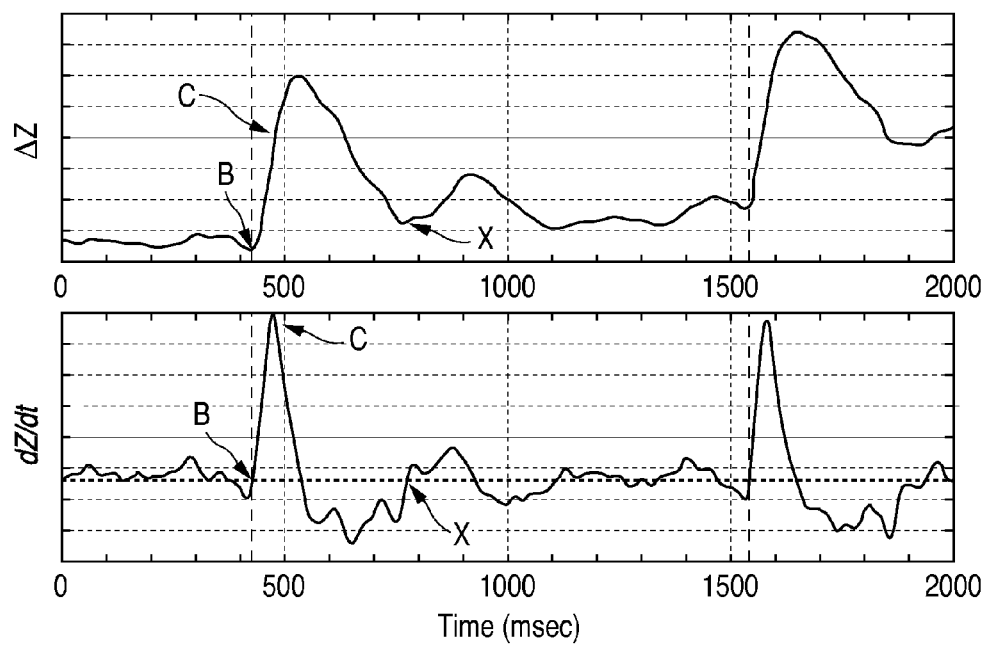
FIG. 3 is a drawing with waveforms showing ΔZ and dZ/dt.

FIG. 3 shows two (2) waveforms. The upper waveform, $\Delta Z$, and the lower waveform dZ/dt emphasize three fiducial points: 1) Point B represents the onset of flow; 2) point C represents the peak systolic upslope or peak time rate of change of the impedance pulse waveform, namely, transradioulnar $dZ/dt_{max}$; and 3) point X represents termination or end of flow, which is the second zero crossing after point C ($dZ/dt_{max}$). The temporal interval between point B and point X represents systolic flow time ($T_{SF}$), the time during which forward SV is measured.

Figure 4:
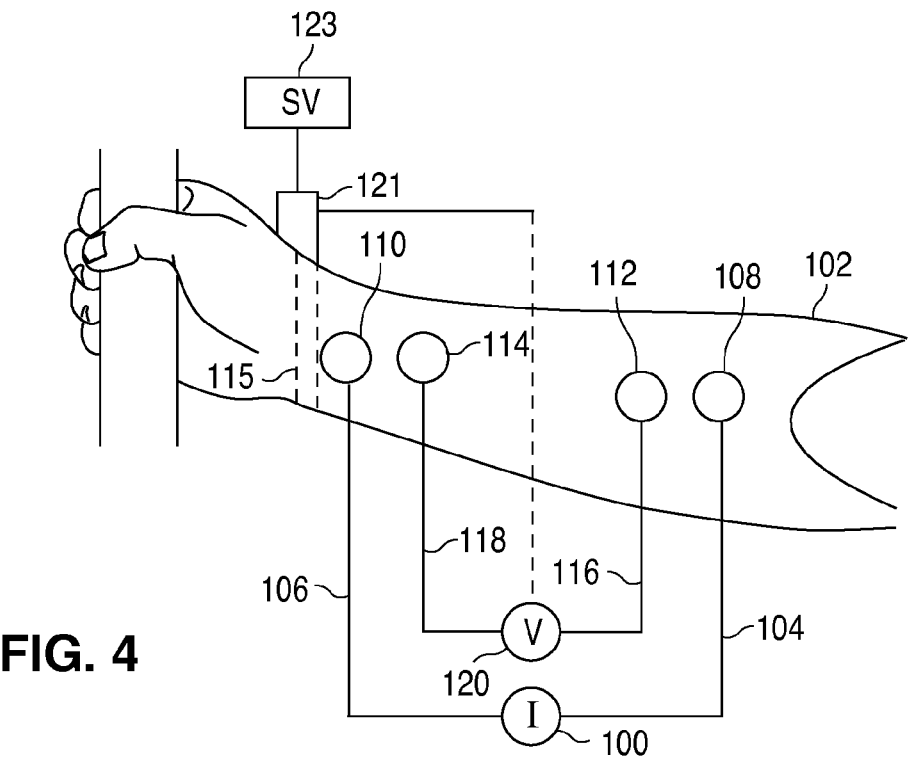
FIG. 4 is a plan view showing the current flow electrodes applied to the person's forearm.

FIG. 4 shows a person's forearm 102 with two spaced apart current flow electrodes 108,110, a first current flow electrode just distal to the antecubital fossa, proximally 108, and a second current flow electrode placed distally and proximal the wrist 110. Between the first and second two spaced-apart current flow electrodes 108,110 are the two spaced-apart voltage sensing electrodes 112,114, the first voltage sensing electrode 112 below the antecubital fossa and distal to the first current flow electrode 108 and the second voltage sensing electrode 114 placed near the wrist, proximal and cephalad to the second current flow electrode 110. Shown is a wrist-worn device (115) (e.g. a band that is configured to wrap around and secure to the wrist) and within, a battery powered current flow generator 100. The current flow generator is operably connected to two current flow electrode wires 104, 106, the first current flow wire 104 operably connected to the first current flow electrode 108 proximal the antecubital fossa, and the second current flow electrode wire 106 operably attached to the second current flow electrode 110. Voltage sensing electrodes 112, 114, proximal the respective current flow electrodes 108, 110 are operably connected to the two voltage sensing wires 116, 118, where the first voltage sensing wire 116 is operably connected to the first voltage sensing electrode 112 and the second voltage sensing wire 118 operably connected to the second voltage sensing electrode 114. Voltage sensing wires 116,118 are fed into the voltmeter 120 operably connected to a signal-processing unit 121, the signal-processing unit yielding a value for SV 123.

Figure 5:
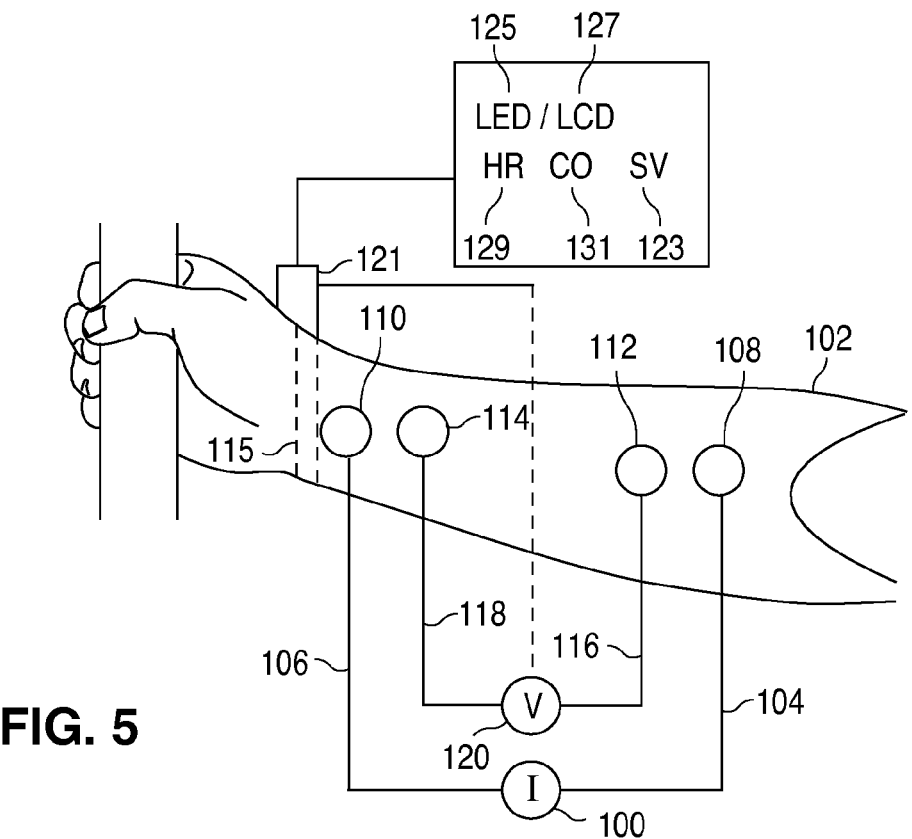
FIG. 5 is a plan view showing the current flow electrodes applied to the person's forearm, and an LED/LCD output display.

FIG. 5 shows a person's forearm 102 with current flow generator 100 operably connected to current flow electrode wires 104,106, which are operably connected to current flow electrodes 108,110, respectively. Voltage sensing electrodes 112, 114 are operably connected to voltage sensing wires 116, 118, respectively, which are operably connected to a voltmeter 120. The voltmeter 120 is operably connected to a signal-processing unit 121 of a wrist-worn device 115, where the signal-processing unit 121 is placed inside the wrist-worn device 115. The wrist-worn device 115 externally shows a view screen with light emitting diode (LED) 125 or a liquid crystal device (LCD) 127, the LED/LCD displaying a value for stroke volume 123, heart rate 129, and cardiac output 131.

Figure 6:
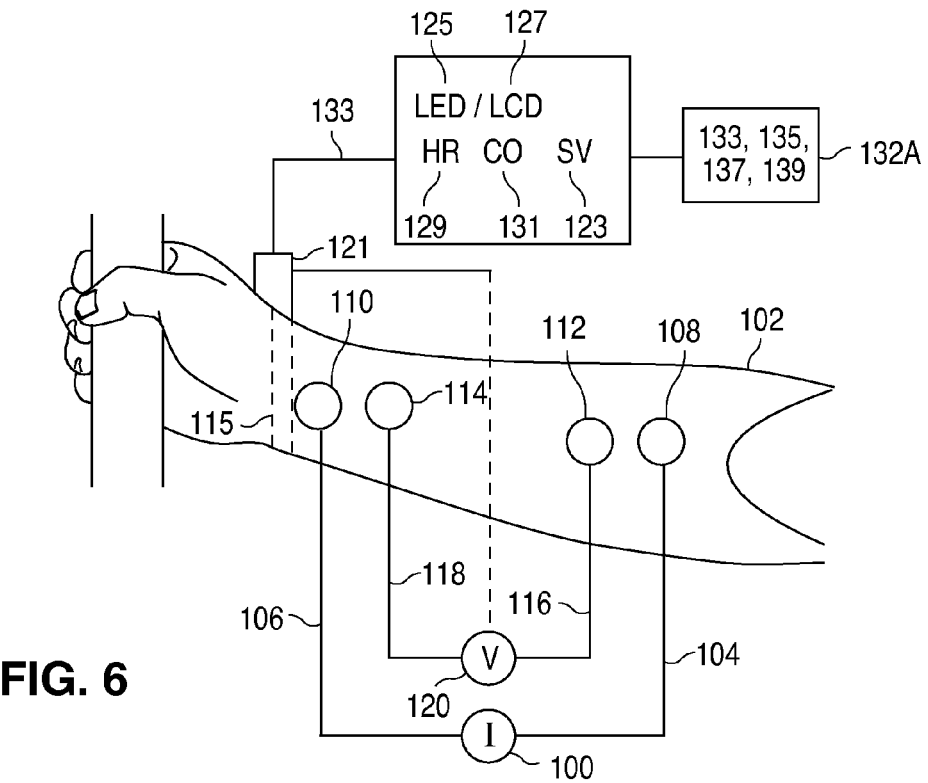
FIG. 6 is a plan view showing the current flow electrodes applied to the person's forearm, and an LED/LCD output display and exercise machine.

FIG. 6 additionally shows a cable 133 operably connected to multi-parameter view screen 125, 127 of an exercise machine 132-A, the exercise machine being a stationary bicycle 133, treadmill 135, elliptical pedaling device 137, a stair-climb machine 139, or equivalent machine. The multi-parameter view screen 125,127 displays values for SV 123 HR 129 and CO 131.

Figure 7:
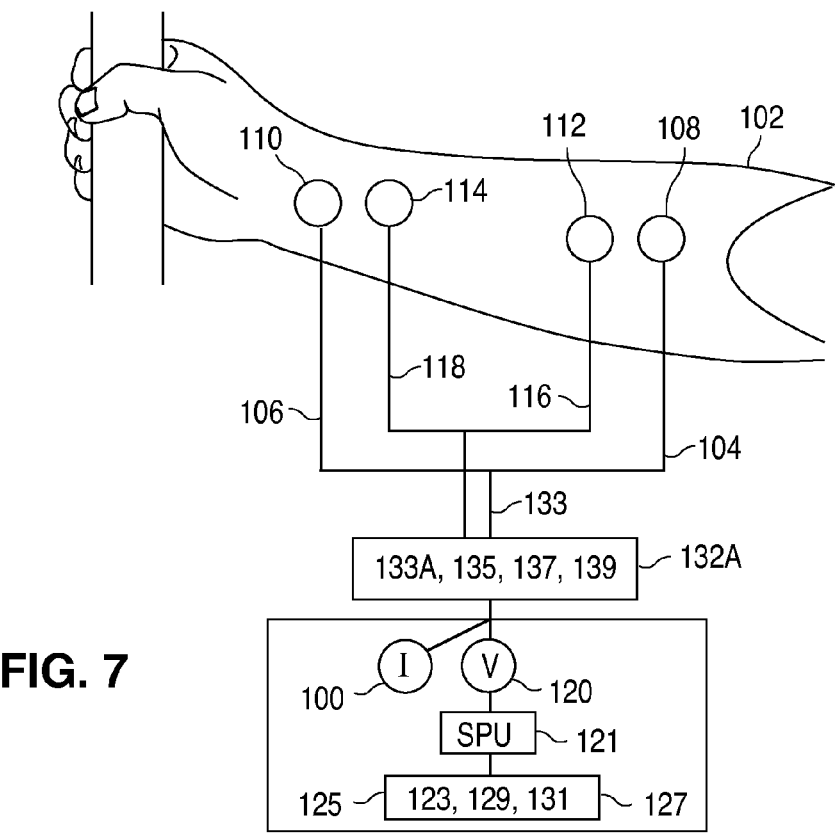
FIG. 7 is a plan view showing the current flow electrodes applied to the person's forearm, and an output display of an exercise machine.

FIG. 7 additionally shows a cable 133 connecting the wires 104/106 to a current flow generator 100 incorporated as part of the exercise machine 132-A, and connecting wires 116, 118 to the voltmeter 120 incorporated as part of the exercise machine 132-A. The signal processing unit 121 also attached to the exercise machine 132-A is connected to the view screen 125, 127 of the exercise machine for displaying a value for stroke volume 123 (SV), heart rate (HR) 129, and cardiac output (CO) 131.

Figure 8:
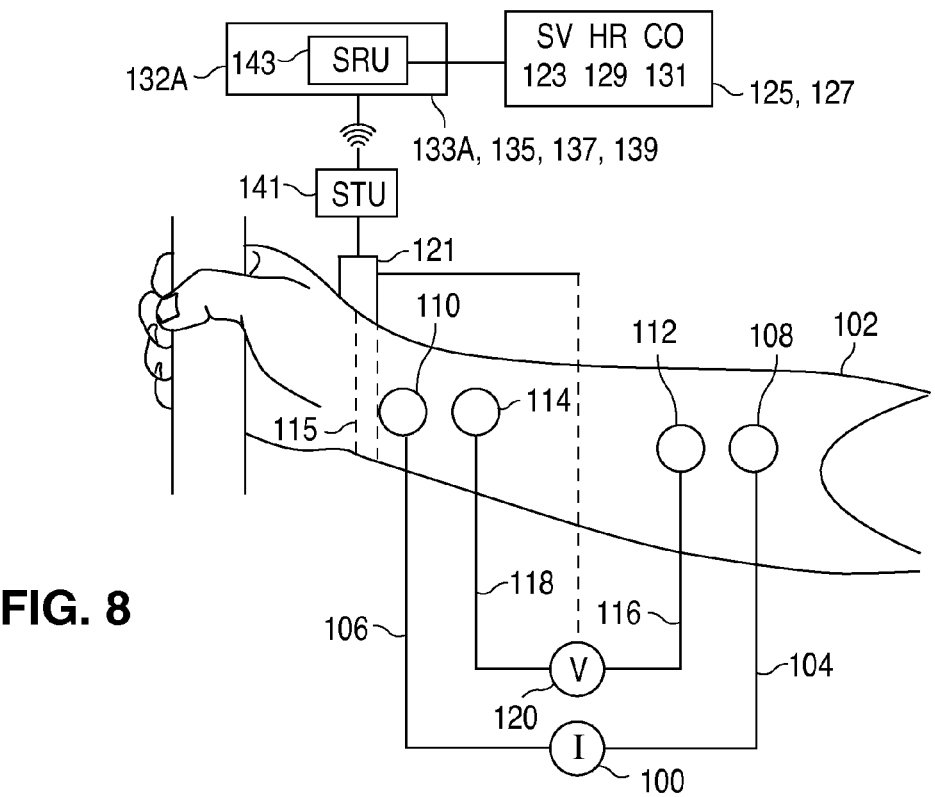
FIG. 8 is a plan view showing the current flow electrodes applied to the person's forearm, and a wireless connection to an output display of an exercise machine.

FIG. 8 additionally shows voltmeter 120 connected to a signal processing unit 121, which is attached to a signal transmission module 141 for wirelessly relaying values for SV 123, HR 129, CO 131 to the signal receiver unit 143 of the exercise machine 132-A so that the view screen (LED/LCD) 125, 127 of the exercise machine 132-A can display values for SV 123, HR 129 and CO 131.

Figure 9:
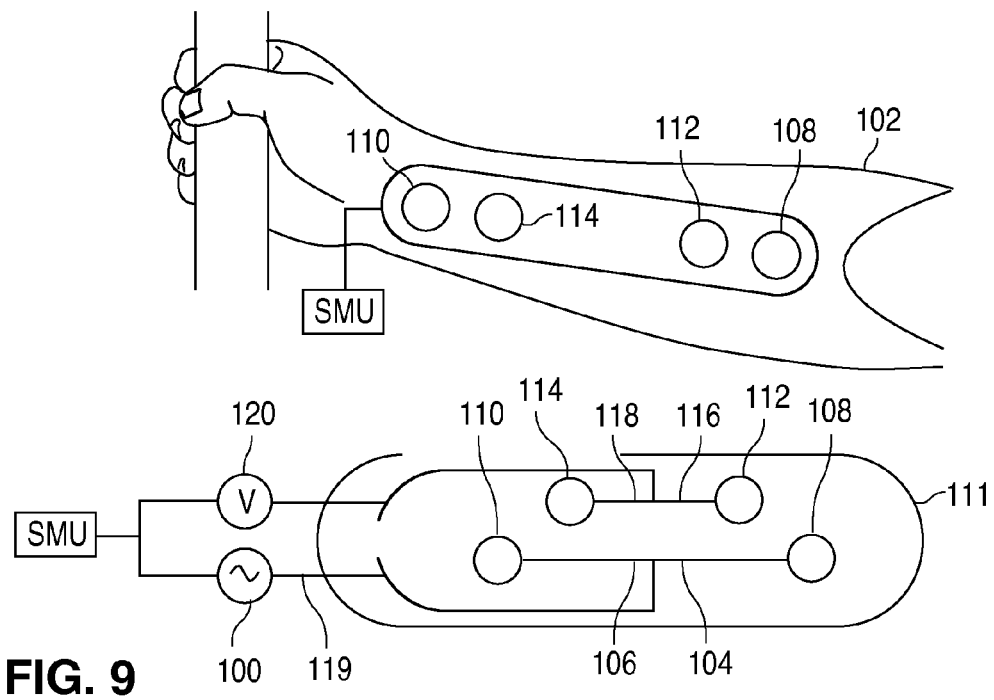
FIG. 9 is a plan view showing the current flow electrodes applied to the person's forearm in the form of an adhesive carrying strip.

FIG. 9 shows a person's forearm 102 where the four electrodes 108, 112, 114, 110 are situated and attached on an adhesive carrying strip 111. The current flow wires 104, 106 and the voltage sensing wires 116, 118 are tethered upon exiting the adhesive electrode strip on single cable 119 that eventually connected to the current flow generator 100 and the voltmeter 120.

The present invention is a method and apparatus for the determination of stroke volume (SV) and cardiac output (CO) by transradioulnar electrical bioimpedance velocimetry, wherein the signal sources are the radial and ulnar arteries of the forearm. SV and CO, while not sensitive indices of the overall intrinsic force generation capacity or contractility of the heart muscle, are the best indicators of the overall performance of the heart considered as a muscular pump. The apparatus and method disclosed involve the application of a constant magnitude alternating current of high frequency and small amplitude across a segment of a person's lower arm (forearm) of the upper extremity to interrogate both the radial and ulnar arteries, considered in the aggregate. The present invention may also provide for calibrating the transradioulnar method and apparatus by determining SV/CO from the transthoracic approach. Thus, in contradistinction to the generally accepted transthoracic bioimpedance method for SV/CO determination, the present invention relates to the acquisition and signal processing of the cardiogenically induced, pulsatile transradioulnar bioimpedance signal for the purpose of SV/CO determination.

Advantages of the transradioulnar method include:
1. Stroke volume (SV) and cardiac output (CO) values are not corrupted by excess extravascular, intrathoracic liquids; namely pulmonary edema fluid.
2. Baseline transradioulnar quasi-static base impedance, $Z_0$, is not substantially affected by pulmonary (lung) ventilation, thereby obviating the necessity the necessity for sophisticated stabilizing adaptive filtering techniques to obtain a steady baseline for measurement of the cardiac-induced transradioulnar impedance change, ΔZ(t), and the magnitudes and fiducial landmarks on its first time-derivative transradioulnar dZ/dt.

3. The cumbersome and user-unfriendly transthoracic electrode montage, and the difficult self-application of the transbrachial electrode configuration, is replaced with a user-friendly 4 spot-electrode montage affixed to an adhesive strip, the adhesive strip affixed to the ventral aspect of the forearm.

4. With the arm at rest, or the arm stabilized by handle bars of a stationary exercise machine, including a bicycle, treadmill, stair-climb, or elliptical pedaling device, motion artifact is limited and is easily filtered by the signal processing module located on the wrist or exercise machine and/or with an integrated tri-axial accelerometer.

5. The bioimpedance signal obtained from the forearm is unaffected by the presence of electronic or metallic devices located on the surface of the chest, or within the chest cavity.

6. Without the perturbing influence of multiple pulsating blood vessels, both arterial and venous, and motion of the heart and chest wall, the signal-to-noise ratio (S/N) of the arterial pulsations of the forearm are enhanced over the various transthoracic bioimpedance methods.

7. The radial and ulnar arteries are more rigid than either the vessels of the chest cavity, including the thoracic aorta, or the brachial artery, thereby yielding a pulsatile velocimetric bioimpedance waveform without the perturbation of vessel volume changes over the cardiac cycle.

As disclosed above, the present invention relates to the measurement of stroke volume (SV) and cardiac output (CO) by means of the transradioulnar method, using the radial and ulnar arteries, in the aggregate, as the cardiogenically induced signal source. Methodologically, the transradioulnar method is similar to the transthoracic and transbrachial techniques for determining SV. However, in the transthoracic technique, signal acquisition is effected over a segment of the thorax (U.S. Pat. No. 7,806,830 B2, FIG. 7) and the transbrachial technique over a segment of the brachium (upper arm) (U.S. Pat. Nos. 7,261,697 B2, 7,740, 590 B2 7,806,830 B2, all three of these patents are incorporated herein by reference for all purposes. In contrast, the transradioulnar technique uses a segment of the lower arm, namely the forearm, for signal acquisition.

FIG. 1 schematically shows one apparatus embodiment according to the present invention, and its electrical interface with a subject's forearm (lower arm) 102. Signal acquisition from the lower arm 102 requires application of a constant magnitude alternating current (A.C.) 100 of high frequency and small amplitude to current flow wires 104 and 106 feeding into current flow electrodes 108 and 110, respectively, that are spaced-apart with the first current flow electrode 108 affixed to the skin of the upper forearm, distal to the antecubital fossa, as well as with the second current flow electrode 110 placed at the lower forearm proximal the wrist, thereby generating a current field between the current flow electrodes 108,110. In the embodiments, the electrodes can be placed on either forearm (left or right).

With the current field thus generated, the potential difference between the current injecting electrodes (AKA alternating current flow electrodes) 108,110 is measured by a voltmeter 120 connected to voltage-sensing wires 116, 118, which are connected, respectively, to voltage sensing electrodes 112 proximal and distal to 108 and 114 placed proximal and cephalad to 110 within the current field. The voltage then passes through differential amplifier 122, then through voltage demodulator 124 whereupon the demodulated voltage undergoes phase adjustment 126. After phase adjustment, and to increase the signal to noise ratio (S/N), the signal is denoised by passage through a first low pass filter 128 (30 Hz). The denoised signal then passes through a high pass filter 130 (0.1 Hz) yielding oscillating signal ΔZ 132, followed by passage through a second low pass filter (10 Hz) 134, yielding quasi-static base impedance signal $Z_0$ 136. Both 132, 136 are then fed into an analog to digital converter (A to D) 138, whereupon the A to D conversion is fed into the signal (micro) processing unit (SMU, SPU) 140 wherein the ΔZ(t) 132 signal is electronically differentiated into its first time-derivative, transradioulnar d(ΔZ(t))/dt, hereafter simply designated as dZ/dt ($\Omega \cdot s^{-2}$), where its peak systolic magnitude is thus designated as $dZ/dt_{max}$ 142. The ratio of $dZ/dt_{max}$ 142 and $Z_0$ 136 undergoes square root transformation $(dZ/dt_{max}/Z_0)^{0.5}$ to yield dimensionless ohmic mean velocity ($s^{-1}$). Systolic flow time ($T_{SF}$, s) 144 is calculated and a volume conductor ($V_C$, mL) 146 is calculated based on person body weight (kg). For the purposes of the invention disclosed herein, $dZ/dt_{max}$ ($\Omega \cdot s^{-2}$) is equivalent to the nadir, or peak negative value of the rate of change of the impedance pulse variation, $dZ/dt_{min}$, where $-dZ/dt_{max} = +dZ/dt_{max} = dZ/dt_{min}$.

In the embodiments of FIGS. 1 and 4 through 8, SV 148,123 is evaluated using equations 1 or 3 below.

$$SV = [a^n \cdot W^b] \cdot \left[ \frac{k_1 k_2}{(dZ/dt_{max} \cdot Z_0^{-1})^{0.5}} \right] \cdot \left[ \frac{dZ/dt_{max}}{Z_0} \right] \cdot T_{SF} \quad \text{Equation (1)}$$

where
- SV=(stroke volume) measured in milliliters (mL),
- a is a real number between 5 and 10 and is a constant for the transradioulnar technique,
- n is an exponent between 2 and 4,
- W is a persons body mass (weight, W) in kg,
- b is an exponent between 1 and 2,
- $k_1$ and $k_2$ collectively are a dimensionless constant at least 0.04 and no greater than 0.3, which can be broken down further as an impedance constant $k_1$ ($s^{-1}$) ranging between 0.08 and 0.2, and a calibrating temporal constant $k_2$ (s) ranging between 0.5 and 1.5.
- $dZ/dt_{max}$ is the peak time rate of change of the transradioulnar impedance pulse variation ($\Omega \cdot s^{-2}$),
- $Z_0$ is the transradioulnar quasi-static base impedance ($\Omega$), $(dZ/dt_{max} \cdot Z_0^{-1})^{0.5} = s^{-1}$, and
- $T_{SF}$ is systolic flow time (seconds, s).

In the preferred embodiment;
The first bracketed term, $a^n W^b$ is an allometric expression relating a person's weight (W) to a constant of proportionality, "$a^n$" where n reflects the magnitude of constant "a" and, except by magnitude, corresponds to the $V_C$ in U.S. Pat. Nos. 7,261,697 B2, 7,740,590 B2, and 7,806,830 B2.

The product of an $a^n W^b$ represents the volume conductor ($V_C$, mL) and, Except by magnitude, corresponds to the $V_C$ in U.S. Pat. Nos. 7,261,697B2, 7,740,590 B2, and 7,806,830 B2.

$$\frac{k_1 k_2}{\sqrt{dZ/dt_{max} \cdot Z_0^{-1}}},$$

the second bracketed term, is a calibrating factor to correct measured $dZ/dt_{max}/Z_0$ for accurate SV determination. The constant "$k_1$" ($s^{-1}$) is an impedance constant, such that when the denominator is $<k_1$, the corrected value of $dZ/dt_{max}/Z_0$ will be greater than uncorrected $dZ/dt_{max}/Z_0$. If the denominator is $>$"$k_1$", then the corrected value of $dZ/dt_{max}/Z_0$ will be less than the measured $dZ/dt_{max}/Z_0$. $K_2$ is a temporal calibrating constant.

$dZ/dt_{max}/Z_0$, the third bracketed term, is the measured (uncorrected) value for $dZ/dt_{max}/Z_0$.

The product of the second and third bracketed terms represents a corrected value for $dZ/dt_{max}/Z_0$.

Hence, $$\left[\frac{k_1 k_2}{\sqrt{dZ/dt_{max} \cdot Z_0^{-1}}}\right] \times [\text{measured } dZ/dt_{max}/Z_0] = \text{corrected } dZ/dt_{max}/Z_0.$$

Corrected $dZ/dt_{max}$ may be modified for heart rate (HR) by a factor of $(HR/60)^n$, where $0.1 < n \leq 1$.

$T_{SF}$ represents systolic flow time (s).

The three (3) bracketed terms are then multiplied by $T_{SF}$ (s) to yield SV (mL).

Equation 1, with exception of magnitude and theoretical foundation for the $V_C$, and correction for measured $dZ/dtmax/Z_0$, is thus analogous to the Sramek-Bernstein equation (U.S. Pat. No. 6,511,438, which is incorporated herein by reference for all purposes) with correction that enables accurate SV determination from the forearm:

$$SV = V_C \cdot (\text{corrected } dZ/dt\text{max}/Z_0) \cdot T_{LVE} \text{ (i.e. } T_{SF}) \qquad \text{Equation (2)}$$

Alternatively, the SV of the left ventricle can be evaluated using the skeleton of the equations found in the transthoracic method (U.S. Pat. No. 6,511,438 B2), and transbrachial method (U.S. Pat. No. 7,261,697 B2, U.S. Pat. No. 7,261, 697 B2, U.S. Pat. No. 7,806,830 B2); the difference being the magnitude of the volume conductor and the site of signal acquisition (forearm, vs. thorax and brachium).

$$SV = V_C \cdot \sqrt{\frac{dZ/dt_{max}}{Z_0}} \cdot T_{SF} \qquad \text{Equation (3)}$$

where,

SV=SV obtained by means of the transradioulnar technique (mL), $V_C$=Volume conductor specific to the forearm technique (mL), which is given as $cM^d$, where c is within the range of 30 to 50, M is the person's weight (kg) and d is in within the range of 1 to 2.

$(dZ/dt_{max} \cdot Z_0^{-1})^{0.5}$=dimensionless ohmic equivalent of mean velocity ($s^{-1}$), where transthoracic $(dZ/dt_{max} \cdot Z_0^{-1})^{0.5}$>transbrachial $(dZ/dt_{max} \cdot Z_0^{-1})^{0.5}$>transradioulnar $(dZ/dt_{max} \cdot Z_0^{-1})^{0.5}$, $T_{SF}$=systolic flow time (s), and Using equation 3, $(dZ/dt_{max}/Z_0)^{0.5}$ may be modified for heart rate (HR) by a factor of $(HR/60)^n$, where $0.1 < n \leq 1$.

Using equations 1 or 3 to determine SV 148, cardiac output (CO) 150 is determined by the product of 148 and heart rate (HR) 152. An accelerometer 154 within the SMU 140 is implemented to detect and stabilize motion artifacts in $Z_0$ 136 and $\Delta Z$ 132.

Many different methods of applying the electrodes or electrode arrays to the forearm are envisioned, such as spot electrodes, arm bands, both circumferential and non-circumferential, adhesive strips, or other attachment means known to the art. In the preferred embodiment, however, four (4) spot-electrodes are affixed to the forearm by means of attachment to an adhesive carrier strip (see FIG. 9), or, alternatively, independently spaced-apart with separated electrode patches. The voltages measured by the voltmeter 120 contains not only a signal caused by the AC applied, but may also contain a signal component from which an electrocardiogram (ECG) can be derived (Lynn W D et al. Arm and wrist surface potential mapping for wearable ECG rhythm recording devices: a pilot study. *J Phys: Conf Ser* 2013; 450, and Goncalves S et al. Non-contact wearable single forearm cardiac biopotential acquisition device. *J Phys: Conf Ser* 3013; 459). The application of filters separates the AC related and ECG related signal components. The apparatus may also contain a data input device. The input device may be any suitable device that provides information to the apparatus, such as a person's age, height, weight, and gender. The input device may also receive information from external sources, such as the ECG or even information from a pulse oximeter located on the forearm (reflectance oximeter) or on a finger (transmittance oximeter). The signal microprocessor 140 is in communication with the data input device, the alternating current source 100, current flow electrodes 108,110, the voltage-sensing electrodes 112,114 and voltmeter 120. The processor (SMU, SPU) 140 is capable of receiving the information and calculating the stroke volume 148 and cardiac output 150 of a person. The stroke volume and cardiac output of the person may be displayed on a view screen on a wrist-worn device or sent by cable or wirelessly via the data output device of the apparatus to a peripheral view screen FIGS. 5, 6, 7, 8.

To better understand the biological electronic circuitry, a second embodiment of the invention FIG. 2 shows a schematic circuit diagram with an AC input (I(t)) to a body part, namely the forearm. An AC field is applied to the total impedance of the forearm (Z(t)) between the voltage sensing electrodes. The forearm impedance further comprises the static tissue impedances (muscle, fat, nerves, vascular tissue, bone) $Z_t$, an impedance compartment comprising interstitial tissue water ($Z_w$) and an impedance compartment comprising the blood ($Z_b$) resistance. They are all added electrically in parallel, comprising the quasi-static base impedance $Z_0$. In parallel with $Z_0$ is the dynamic, time-dependent, cardiogenically induced component of the blood resistance $\Delta Z_b(t)$ (i.e. $\Delta Z$). Excluding the respiratory component of Z, the parallel connection of $Z_0$ and $\Delta Z_b(t)$ constitutes the total forearm impedance Z(t) between the voltage-sensing electrodes. The dot product of I(t) and Z(t) yields a static voltage $U_0$ and an oscillating voltage U(t). As pertains to parallel electronic circuitry for AC, the impedances are added as their reciprocals:

$$I(t) \cdot [(\|Z_t\|Z_b\|Z_w)\|\Delta Z_b(t)] = U_0\|\Delta U_b = I$$
$$(t) \cdot [Z_0\|\Delta Z(t)] = U_0\|\Delta U(t) \qquad \text{Equation (4)}$$

In a third embodiment, FIG. 3 shows two (2) waveforms; the upper waveform, labeled $\Delta Z$, is the time-dependent impedance pulse variation over a segment of forearm undergoing electrical interrogation, wherein point B represents the onset of flow over the segment of forearm interrogated, point C represents the maximum systolic forward upslope of the cardiogenically-induced impedance change, and point X represents the end of flow of the interrogated segment of forearm. The temporal interval from point B to point X is the systolic flow time ($T_{SF}$). The lower waveform, labeled dZ/dt, is the first time-derivative (time rate of change) of ΔZ, wherein point B represents the onset of flow in the segment of forearm under electrical interrogation, point C represents the peak rate of change of the upslope of ΔZ, which is $dZ/dt_{max}$, and point X which represents the end of flow in the segment of forearm undergoing electrical interrogation. The temporal interval between point B and point X of the dZ/dt waveform represents the systolic flow time $T_{SF}$ over the forearm segment electrically interrogated. Alternatively, equivalent fiducial landmarks on second time derivative of the impedance change ΔZ, namely $d^2Z/dt^2$, can be implemented to determine $T_{SF}$. It is also envisioned that $T_{SF}$ can be determined by means of the $SpO_2$ curve, or its first time-derivative $d(SpO_2)/dt$ as disclosed in U.S. Pat. Nos. 7,261,697 B2, 7,740,590 B2, and 7,806,830 B2. It is envisioned that the $SpO_2$ signal can be obtained from the earlobe, forehead, or other signal acquisition sites on the body, but in the preferred embodiment the signal may be determined from a fingertip, base of finger or on the forearm. Systolic flow time $T_{SF}$, equivalent to left ventricular ejection time LVET, can be approximated in persons with healthy hearts as:

Male: $T_{SF} = -0.0017 \cdot HR + 0.413$, and

Female: $T_{SF} = -0.0016 \cdot HR + 0.418$.

(Weissler et al. Systolic time intervals in heart failure in man. Circulation 1968; 37:149.)

In a fourth embodiment of the invention, FIG. 4 shows the forearm 102 of the right upper extremity of a person undergoing electrical interrogation. The forearm of the left upper extremity (left upper arm) can be used equivalently. The current flow generator 100 delivers a constant magnitude high frequency (70-100 kHz), small amplitude (2-4 mA) oscillating current (AC) by means of 2 current flow wires 104,106 leading to 2 spaced-apart current flow electrodes 108,110 whereupon a current field is applied to the segment of forearm between the current flow electrodes 108,110. Spaced-apart voltage sensing electrodes 112,114 located proximal the current flow electrodes 108,110 and within the current field direct the voltage via voltage sensing wires 116,118 to a voltmeter 120 located within the signal processing unit 121 operably attached to a wrist-worn device 115, the signal-processing unit capable of calculating a stroke volume (SV) 123, displayed on the view screen of the wrist worn device.

In a fifth embodiment, FIG. 5 shows a person's forearm 102 with current flow electrodes 108,110 operably connected to current flow wires 104,106, which are operably attached to a current flow generator 100 generating a current field between voltage sensing electrodes 112,114 that are operably attached to voltage sensing wires 116,118 feeding into a voltmeter 120. The voltmeter is operably attached to a signal-processing unit 121 of a wrist-worn device 115. The signal-processing unit 121 is placed inside a wrist-worn device 121, the wrist-worn device 121 externally showing a view screen with light-emitting diode (LED) 125 or a liquid crystal display (LCD) 127, the LED/LCD displaying a value for stroke volume (SV) 123, heart rate (HR) 129, and cardiac output (CO) 131.

In a sixth embodiment, FIG. 6 shows a cable 133 operably connected to a multi-parameter view screen 125,127 of an exercise machine 132-A, the exercise machine being a stationary bicycle 133-A, treadmill 135, elliptical pedaling device 137, a stair-climb machine 139, or other similar exercise machine. The multi-parameter view screen 125,127 displays values for SV 123, HR 129, and CO 131.

In a seventh embodiment, FIG. 7 shows a cable 133 connecting the wires 104/106 to a current flow generator 100, and voltage sensing wires 116,118 to voltmeter 120, where the voltmeter 120 and current flow generator 100 are operably connected to the signal processing unit 121 attached to an exercise machine 132-A, where view screen 125,127 of the exercise machine 132-A displays a value for SV 123, HR 129, and CO 131.

In an eighth embodiment, FIG. 8 shows voltmeter 120 connected or housed in the signal receiving unit of the signal processing unit 121. The signal processing unit 121 yielding values for SV 123 HR 129 and CO 131 which are telemetered by a signal transmission unit 141 wirelessly to a signal receiving unit 143 of exercise machine 132-A. The view screen 125,127 attached to the signal-receiving unit 143 displays values for SV 123 HR 129 and CO 131.

In the ninth embodiment, FIG. 9 shows a person's forearm 102 with an adhesive electrode tape 111 applied to the ventral surface of the forearm 102, the adhesive tape attached to embedded current flow electrodes 108,110 current flow wires 104,106 voltage sensing electrodes 112,114 and voltage sensing wires 116,118, the voltage sensing and current flow wires tethered to a cable 119 operably connected to the signal processing unit (SPU) housing the current flow generator 100 and voltmeter 120.

In a tenth and final embodiment, heart rate HR can be determined by the following means:
The SPU can receive, detect and process ECG signals and,
  1. Measure the R-R time intervals of an ECG over a given period of time Δt,
  2. Divide 60 seconds by the average of the R-R time intervals over Δt.
  3. Examples:
     a. If the average R-R time interval is 0.5 seconds over one minute Δt (60 s), then Δt/R-R=60/0.5=120 beats per minute (BPM).
     b. If the average R-R time interval is 0.5 seconds over Δt 15 seconds, then HR=60/Δt×Δt/0.5=60/15×15/0.5=120 BPM.

c. If the average R-R time interval is 2 seconds over one minute Δt (60 s), then the heart rate=60/2=30 BPM.
  d. If the average R-R time interval is 2 seconds over Δt 15 seconds, then HR=60/Δt×Δt/2=60/15×15/2=30 BPM.

The SPU can receive, detect and process ECG signals and,
  1. Measure the number of ECG R wave spikes over a stipulated period of time Δt.
  2. Multiply number of R spikes×60/Δt.
  3. Examples:
     a. If 20 R wave spikes occur in 15 seconds, then 20×60/15=20×4=80 BPM.
     b. If 30 R wave spikes occur in 15 seconds, then 30×60/15=30×4=120 BPM.

The SPU can receive, detect and process $SpO_2$ signals and:
  1. Determine the first time-derivative of $SpO_2$, $d(SpO_2)/dt$,
  2. The first and largest spike of the derivatized waveform $d(SpO_2)/dt_{max}$ can be treated as per the methods outlined and disclosed in U.S. Pat. No. 7,261,697

B2, 7,740,590 B2 and 7,806,830 B2 and treated as in methods using ECG or d(SpO$_2$)/dt.
3. The second time-derivative, d$^2$(SpO$_2$)/dt$^2$ can be used as per methods for d(SpO$_2$)/dt or ECG to determine HR (d(SpO$_2$)/dt$_{max}$ to d(SpO$_2$)/dt$_{max}$ time interval).

The SPU can receive, detect, and process the first or second time derivatives of ΔZ and:
1. The maximum of dZ/dt or d$^2$Z/dt$^2$, which are dZ/dt$_{max}$ or d$^2$Z/dt$^2$$_{max}$, respectively, can be treated as per the method using ECG or d(SpO$_2$)/dt to determine HR.
2. Specifically, the time interval between the maximum systolic peaks (dZ/dt$_{max}$ to dZ/dt$_{max}$) can be treated as per the methods delineated in treatment of ECG or SpO$_2$ signals.

It is to be understood that the present invention is not limited to the embodiment(s) described above and illustrated herein, but encompasses any and all variations falling within the scope of the appended claims. For example, references to the present invention herein are not intended to limit the scope of any claim or claim term, but instead merely make reference to one or more features that may be covered by one or more of the claims. Materials, processes and numerical examples described above are exemplary only, and should not be deemed to limit the claims. Further, as is apparent from the claims and specification, not all method steps need be performed in the exact order illustrated or claimed.

Hardware, software and/or firmware can be used to implement the logic steps and/or processes of the invention. It should further be appreciated that such logic steps or process can be implemented as computer-executable instructions stored on a non-transitory computer readable medium, such a CD or DVD (including re-writable CDs and DVDs), flash or other non-volatile memory, ROM, EEPROM, disc drive, solid state drive, etc.

What is claimed is:

1. An apparatus for determining stroke volume by bioimpedance from a person, comprising:
two or more spaced apart alternating current flow electrodes positionable on a person;
two or more spaced apart voltage sensing electrodes positionable on the person and between the alternating current flow electrodes;
an alternating current source electrically connectable to the alternating current flow electrodes;
a voltmeter electrically connectable to the voltage sensing electrodes and configured to generate a voltage signal from a voltage sensed by the voltage sensing electrodes;
a data input device in communication with the processing unit for receiving the person's weight W;
a processing unit electrically connectable with the voltmeter and configured to determine a stroke volume (SV) using the voltage signal and the following equation:

$$SV = [a^n \cdot W^b] \cdot \left[ \frac{k_1 k_2}{(dZ/dt_{max} \cdot Z_0^{-1})^{0.5}} \right] \cdot \left[ \frac{dZ/dt_{max}}{Z_0} \right] \cdot T_{SF}$$

wherein a is at least 5 and no greater than 10, n is at least 2 and no greater than 4, W is the person's weight, b is at least 1 and no greater than 2, $k_1 \cdot k_2$ collectively are a dimensionless constant at least 0.04 and no greater than 0.3, dZ/dt$_{max}$ is a peak time rate of change of a transradioulnar impedance pulse variation, $Z_0$ is a transradioulnar quasi-static base impedance, $T_{SF}$ is a systolic flow time.

2. The apparatus for determining stroke volume of claim 1, wherein the constant $k_1 \cdot k_2$ comprises:
an impedance constant $k_1$ at least 0.08 and no greater than 0.2, and
a calibrating temporal constant $k_2$ at least 0.5 and no greater than 1.5.

3. The apparatus for determining stroke volume of claim 1, wherein the processor is configured to:
determine heart rate from the voltage signal; and
determine cardiac output (CO) by using the following formula: CO=(heart rate)×(SV).

4. The apparatus for determining stroke volume of claim 3, further comprising:
a band configured to wrap around and secure to a person's wrist, wherein the processing unit is mounted to the band.

5. The apparatus for determining stroke volume of claim 4, further comprising:
a display mounted to the band, wherein the display is electrically connected to the processing unit and configured to display at least one of the determined stroke volume and the determined cardiac output.

6. The apparatus for determining stroke volume of claim 3, further comprising:
an exercise machine being one of a stationary bicycle, a treadmill, an elliptical pedaling device and a stair-climbing machine, wherein the exercise machine includes a display operatively connectable to the processing unit and configured to display at least one of the determined stroke volume and the determined cardiac output.

7. The apparatus for determining stroke volume of claim 6, wherein the operative connection between the display and the processing unit comprises a cable.

8. The apparatus for determining stroke volume of claim 6, wherein the operative connection between the display and the processing unit comprises a wireless connection.

9. The apparatus for determining stroke volume of claim 6, wherein the alternating current source, the voltmeter and the processing unit are mounted to the exercise machine.

10. The apparatus for determining stroke volume of claim 1, further comprising:
an exercise machine being one of a stationary bicycle, a treadmill, an elliptical pedaling device and a stair-climbing machine, wherein the exercise machine includes a display operatively connectable to the processing unit by a wireless connection and configured to display at least one of the determined stroke volume and the determined cardiac output.

11. The apparatus for determining stroke volume of claim 1, further comprising:
an adhesive strip on which the two or more spaced apart alternating current flow electrodes and the two or more spaced apart voltage sensing electrodes are affixed.

12. A method of determining stroke volume by bioimpedance from a person, comprising:
positioning two or more spaced apart alternating current flow electrodes on the forearm of a person;
positioning two or more spaced apart voltage sensing electrodes on the forearm of the person and between the alternating current flow electrodes;
providing an alternating current flow through the alternating current flow electrodes;
measuring a voltage between the voltage sensing electrodes;

determining a stroke volume (SV) using the measured voltage and the following equations:

$$SV = [a^n \cdot W^b] \cdot \left[\frac{k_1 k_2}{(dZ/dt_{max} \cdot Z_0^{-1})^{0.5}}\right] \cdot \left[\frac{dZ/dt_{max}}{Z_0}\right] \cdot T_{SF}$$

wherein a is at least 5 and no greater than 10, n is at least 2 and no greater than 4, W is the person's weight, b is at least 1 and no greater than 2, $k_1 \cdot k_2$ collectively are a dimensionless constant at least 0.04 and no greater than 0.3, $dZ/dt_{max}$ is a peak time rate of change of a transradioulnar impedance pulse variation, $Z_0$ is a transradioulnar quasi-static base impedance, $T_{SF}$ is a systolic flow time.

13. The method of claim 12, wherein the positioning of the two or more spaced apart alternating current flow electrodes on the forearm of the person comprises:
positioning a first of the two or more spaced apart alternating current flow electrodes proximal to the antecubital fossa of the person's forearm; and
positioning a second of the two or more spaced apart alternating current flow electrodes proximal to the wrist of the person.

14. The method of claim 12, wherein the constant $k_1 \cdot k_2$ comprises:
an impedance constant k1 at least 0.08 and no greater than 0.2, and
a calibrating temporal constant k2 at least 0.5 and no greater than 1.5.

15. The method of claim 12, further comprising:
determining heart rate from the measured voltage; and
determining cardiac output (CO) by using the following formula:

CO=(heart rate)×(SV).

16. The method of claim 15, further comprising:
displaying at least one of the determined stroke volume (SV) and the determined cardiac output (CO) on a visual display.

17. The method of claim 16, further comprising:
mounting the visual display to the person's wrist.

18. The method of claim 16, wherein the visual display is included as part of an exercise machine being one of a stationary bicycle, a treadmill, an elliptical pedaling device and a stair-climbing machine.

19. The method of claim 12, wherein the two or more spaced apart alternating current flow electrodes and the two or more spaced apart voltage sensing electrodes are affixed to an adhesive strip.

* * * * *